(12) United States Patent
Lee, Jr.

(10) Patent No.: US 7,311,834 B2
(45) Date of Patent: Dec. 25, 2007

(54) APPARATUS FOR THE TREATMENT OF PARTICULATE BIODEGRADABLE ORGANIC WASTE

(75) Inventor: John W Lee, Jr., Bellevue, WA (US)

(73) Assignee: CH2M Hill, Inc., Englewood, CO (US)

( * ) Notice: Subject to any disclaimer, the term of this patent is extended or adjusted under 35 U.S.C. 154(b) by 0 days.

(21) Appl. No.: 11/586,343

(22) Filed: Oct. 25, 2006

(65) Prior Publication Data

US 2007/0095734 A1 May 3, 2007

Related U.S. Application Data

(63) Continuation of application No. 11/146,426, filed on Jun. 6, 2005, now abandoned, which is a continuation of application No. 10/286,454, filed on Oct. 31, 2002, now Pat. No. 6,905,600.

(60) Provisional application No. 60/339,846, filed on Nov. 16, 2001, provisional application No. 60/366,389, filed on Mar. 21, 2002.

(51) Int. Cl.
*C02F 3/28* (2006.01)

(52) U.S. Cl. ...................... 210/603; 210/612; 210/631; 210/175; 210/198.1; 210/202; 210/259; 435/262.5; 71/10

(58) Field of Classification Search ................ 210/603, 210/612, 613, 631, 173, 175, 181, 198.1, 210/205, 206, 209, 252, 259, 202; 435/262, 435/262.5; 71/10
See application file for complete search history.

(56) References Cited

U.S. PATENT DOCUMENTS

| | | | |
|---|---|---|---|
| 3,711,392 A | 1/1973 | Metzger | |
| 3,933,628 A | 1/1976 | Varani | |
| 3,959,125 A | 5/1976 | Teletzke | |
| 4,022,665 A | 5/1977 | Ghosh et al. | |

(Continued)

FOREIGN PATENT DOCUMENTS

DE    199 37 876 A1    3/2001

(Continued)

OTHER PUBLICATIONS

Davis & Cornwell (1991) Introduction to Environmental Engineering 2nd Edition, McGraw-Hill, Inc., pp. 393-396.

(Continued)

*Primary Examiner*—Fred G. Prince
(74) *Attorney, Agent, or Firm*—Swanson & Bratschun, LLC

(57) ABSTRACT

An apparatus for treating particulate biodegradable organic waste includes a thermal hydrolysis reactor receiving the particulate biodegradable organic waste for performing thermal hydrolysis at a temperature of about 130° C. at a pressure at or above the saturated water vapor pressure of the organic waste to produce a slurry including solubilized organic material and residual solids. A pH adjustment means for adjusting the pH of the particulate biodegradable organic waste as necessary to provide an acidic pH of greater than about 3.15 before thermo hydrolysis of the particulate biodegradable organic waste is provided. Separating means receive the solubilized organic material and residual solids for separating solubilized organic material from the residual solids. An anaerobic reactor is configured to receive the solubilized organic material.

4 Claims, 3 Drawing Sheets

U.S. PATENT DOCUMENTS

| | | |
|---|---|---|
| 4,318,993 A | 3/1982 | Ghosh et al. |
| 4,551,250 A | 11/1985 | Morper |
| 4,597,872 A | 7/1986 | Andersson et al. |
| 4,652,374 A | 3/1987 | Cohen |
| 4,765,900 A * | 8/1988 | Schwoyer et al. .......... 210/603 |
| 4,846,964 A | 7/1989 | Scott |
| 4,861,519 A | 8/1989 | Tusa et al. |
| 4,975,106 A | 12/1990 | Ferguson |
| 5,057,220 A | 10/1991 | Harada |
| 5,120,448 A | 6/1992 | Dorica |
| 5,169,532 A | 12/1992 | Whitlock |
| 5,266,201 A | 11/1993 | Letourneux |
| 5,269,947 A | 12/1993 | Baskis |
| 5,279,637 A | 1/1994 | Lynam et al. |
| 5,360,553 A | 11/1994 | Baskis |
| 5,366,558 A * | 11/1994 | Brink ........................ 127/43 |
| 5,377,917 A | 1/1995 | Wiljan et al. |
| 5,393,428 A * | 2/1995 | Dilla et al. ................ 210/631 |
| 5,407,817 A | 4/1995 | Lightsey |
| 5,431,819 A | 7/1995 | Hack et al. |
| 5,525,229 A | 6/1996 | Shih |
| 5,529,692 A | 6/1996 | Kubler |
| 5,543,061 A | 8/1996 | Baskis |
| 5,707,417 A | 1/1998 | Yokoyama et al. |
| 5,766,440 A * | 6/1998 | Ino et al. .................... 205/99 |
| 5,773,526 A | 6/1998 | Van Dijk et al. |
| 5,888,307 A | 3/1999 | Solheim |
| 6,296,766 B1 | 10/2001 | Breckenridge |
| 6,342,378 B1 | 1/2002 | Zhang |
| 6,387,221 B1 | 5/2002 | Schoenhard |
| 6,464,875 B1 | 10/2002 | Woodruff |

FOREIGN PATENT DOCUMENTS

| | | |
|---|---|---|
| EP | 0 335 825 A1 | 10/1989 |
| JP | 4-326998 A | 11/1992 |
| JP | 10-192898 A | 7/1998 |
| JP | 10-235315 A1 | 9/1998 |
| WO | WO 88/04282 | 6/1988 |

OTHER PUBLICATIONS

Garvie (1992) TAPPI Proceedings 1992 Environmental Conference, pp. 681-685, Anaerobic/Aerobic Treatment of NSSC/CTMP Effluent and Biotags Utilization.

Lee (2000) Industrial Environmental Control Pulp and Paper Industry 3rd Edition, Edited by Allan M. Springer, TAPPI Press, pp. 369-416.

Lemley (2003) Discover.com 24:51-57.

Smith (1994) TAPPI Proceedings 1994 International Environmental Conference, pp. 153-156.

* cited by examiner

APPARATUS FOR THE TREATMENT OF PARTICULATE BIODEGRADABLE ORGANIC WASTE

RELATED APPLICATIONS

This application is a continuation of U.S. patent application Ser. No. 11/146,426, filed Jun. 6, 2005, abandoned, which is a continuation of U.S. patent application Ser. No. 10/286,454, filed Oct. 31, 2002, now U.S. Pat. No. 6,905,600, both entitled "Method And Apparatus For The Treatment Of Particulate Biodegradable Organic Waste," which claims priority from U.S. Provisional Patent Application Ser. No. 60/339,846, filed on Nov. 16, 2001, entitled "Method and Apparatus for the Thermal Hydrolysis and Anaerobic Treatment of Particulate Biodegradable Organic Waste" and from U.S. Provisional Patent Application Ser. No. 60/366,389, filed on Mar. 21, 2002, entitled "Method and Apparatus for the Thermal Hydrolysis and Anaerobic Treatment of Particulate Biodegradable Organic Waste," each of which in incorporated by reference herein.

FIELD OF THE INVENTION

This invention is directed to an apparatus for the treatment of particulate biodegradable organic waste, and more particularly to an apparatus for the thermal hydrolysis and anaerobic treatment of particulate biodegradable organic waste.

BACKGROUND OF THE INVENTION

A number of countries in Asia and in Europe currently require or are expected to require biodegradable solid waste and food waste solids from residences, as well as restaurants and institutions that prepare and serve food, to be source segregated from metal, glass, plastics, paper, and other solid waste materials. This regulatory trend is likely to be adopted by larger cities in both the United States and Canada. Currently, disposal of food waste-solids in these countries is by landfill, incineration and to a limited degree composing to produce soil amendment.

South Korea is one representative country seeking to restrict disposal of food waste and biodegradable solid waste. The Korean national government has indicated it intends to prohibit landfill disposal of food wastes by Jan. 1, 2006, and ocean dumping of wastewater treatment biosolids by Jan. 1, 2004. Food wastes are composed primarily of vegetables, fruits, grains, and meat/fish products that contain fiber, carbohydrate, fat, protein and inorganic ash. Data indicates that Korean source segregated food wastes contain 76-84% moisture and 16-24% dry matter. Additionally, the dry matter is 80-90% volatile. Incineration is a costly alternative, skeptically viewed by the Korean public because of environmental concerns.

As an alternative to conventional landfill or incineration disposal, particulate food wastes, wastewater treatment biosolids, and other biodegradable organic particulate matter (i.e. manure, green wastes, source separated biodegradable municipal solid waste, etc.) can be first solubilized by thermal hydrolysis, with the liquid fraction converted, under suitable anaerobic conditions to methane gas and carbon dioxide. The residual carbonaceous material containing nitrogen and phosphorus is suitable for use as a soil amendment or as a fertilizer with further nitrogen and phosphorus fortification. Alternatively, the residual carbonaceous material has sufficient caloric value so as to be suitable for use as a source of fuel to generate energy.

Thus, thermal hydrolysis of particulate biodegradable organic wastes followed by anaerobic conversion of the solubilized fraction of these organic solid wastes potentially provides an economically attractive and environmentally sound disposal alternative offering significant benefits.

Yokoyama, U.S. Pat. No. 5,707,417, is directed to a method for treating garbage including thermal hydrolysis followed by anaerobic digestion. More particularly, Yokoyama is concerned with the treatment of garbage resulting from the preparation, cooking and dispensing of food containing water-insoluble organic compounds. Yokoyama teaches thermal hydrolysis of food waste for periods of 1-720 minutes at temperatures between 100-400° C. (212-752° F.) and at pressures higher than the corresponding water vapor saturation pressure (2-200 atm or 29.4-2940 psig). Following solubilization, the solubilized organics and insoluble particulates are anaerobically digested to produce methane. Yokoyama further teaches that the soluble and insoluble products from thermal hydrolysis may be separated before subjecting the liquid phases to anaerobic digestion. Yokoyama then teaches that the solid phases can be recovered and burned or processed into compost. While Yokoyama provides considerable benefit over conventional landfill or incineration disposal of food wastes, the process taught by Yokoyama is not energy efficient, nor does it maximize solubilization or liquid removal from solid phases. Further, Yokoyama does not minimize the soluble fraction recalcitrant to biodegradation or ammonia produced from thermal hydrolysis.

Solheim, U.S. Pat. No. 5,888,307, teaches a continuous multi-stage system consisting of four steam reaction vessels operated in series to solubilize organic waste materials, including sewage sludge. Solheim teaches that to minimize heating costs and to conserve energy, flash steam from the fourth stage reaction vessel can be combined with supplemental steam to heat the first stage reaction vessel. In addition, flash steam from the third stage reaction vessel can be used to heat the second stage reaction vessel. Solheim teaches the hydrolysis occurs in a temperature range of 160-240° C. (320-464° F.). Solheim further teaches that acid can be added in order to obtain enhanced hydrolysis. Solheim fails to optimize energy usage in the hydrolysis process. Furthermore, Solheim does not teach any benefit in separating solubilized organics and residual solids before anaerobic digestion.

Shih, U.S. Pat. No. 5,525,229, teaches an apparatus and method for anaerobic digestion of organic materials such as sewage sludge, municipal waste, animal waste and other highly organic materials. Shih discloses bacterial hydrolysis of such waste prior to anaerobic digestion to enhance soluble organics available for anaerobic digestion. Shih also teaches recycling heat from the digestion process to preheat materials being added to the hydrolysis step. The bacterial hydrolysis step taught by Shih fails to provide sufficient solubilization and solids dewatering potential to minimize the volume of residual solids. It, therefore, is not fully effective at minimizing the volume of solid wastes which must be disposed of.

The present invention is intended for overcoming one or more of the problems discussed above.

SUMMARY OF THE INVENTION

A first aspect of the present invention is a method of treating particulate biodegradable organic waste. The term particulate biodegradable organic waste includes, but is not limited to, food waste, wastewater treatment biosolids, source separated biodegradable municipal solid waste, and yard and garden ("green") wastes. The method includes the step of adjusting the pH of the biodegradable organic waste as necessary to provide an acidic pH and subjecting the particulate biodegradable organic waste with an acidic pH to thermal hydrolysis at a temperature of greater than about 130° C. and a pressure at or above the saturated water vapor pressure, and preferably at a temperature of about 170° C. or greater and a pressure of about 120 psig or greater, to produce a slurry including solubilized organic material and residual solids. The solubilized organic material is separated from the residual solids and subjected to anaerobic digestion to produce a methane rich gas. The temperature of the hydrolysis is preferably above about 130° C. and within a range of between about 170°-225° C. while the pressure is preferably above about 46.1 psig and between about 120-366 psig. The method may further include heating the particulate biodegradable organic waste with the separated solubilized organic material prior to thermal hydrolysis. An anaerobic reactor is operatively associated with the first liquid/solid separator to receive the liquid separated from the particulate biodegradable organic waste to produce a methane rich gas.

In a preferred embodiment, the thermal hydrolysis reactor is a steam hydrolysis reactor. In such an embodiment the apparatus further includes a pre-steaming bin receiving the deliquified particulate biodegradable organic waste from the first liquid/solid separator and providing the deliquified particulate biodegradable organic waste to the steam hydrolysis reactor. A steam flash tank receives solubilized organic material and residual solids from the steam hydrolysis reactor. A steam recovery circuit operatively associated with the pre-steaming bin and the steam flash tank recycles steam recovered from the steam flash tank to the pre-steaming bin.

A source of dilution water may be operatively associated with the anaerobic reactor for diluting the liquid separated from the particulate biodegradable organic waste. The source of diluting water may be a secondary wastewater treatment plant effluent. A particle sizer is preferably provided for sizing the particulate biodegradable organic waste to below a select particle size before the particulate biodegradable waste is subject to thermal hydrolysis. Residual solids separated from the solubilized organic material is preferably subjected to composing. Also in a preferred embodiment, the waste is sized between 0.25"-2.0" particles. The heat for the thermal hydrolysis may be provided by steam. Preferably the particulate biodegradable organic waste is heated with the solubilized organic material by mixing the solubilized organic material with the particulate biodegradable organic waste. After the mixing step, the liquid, including the solubilized organic material, is removed from the preheated particulate biodegradable organic waste and this removed liquid is then subjected to anaerobic digestion. The method may then further include recycling residual steam from the thermal hydrolysis step to the particulate biodegradable organic waste prior to thermal hydrolysis to preheat the particulate biodegradable organic waste.

A second aspect of the present invention is a method of treating particulate biodegradable organic waste including subjecting the particulate biodegradable organic waste to thermal hydrolysis at temperatures preferably of about 130° C. or greater at a pressure preferably at about or above the saturated water vapor pressure, to produce a slurry including solubilized organic material and residual solids. The solubilized organic material is separated from the residual solids. Prior to the thermal hydrolysis step, the particulate biodegradable organic waste is heated using the separated solubilized organic material. After this preheating step and before the thermal hydrolysis step, liquid, including the solubilized organic material, is removed from the preheated particulate biodegradable organic waste and is subjected to anaerobic digestion to produce a methane rich gas.

Yet another aspect of the present invention is an apparatus for treating particulate biodegradable organic waste. The apparatus includes a feed blend tank receiving the particulate biodegradable organic waste. A first liquid/solid separator receives the particulate biodegradable organic waste from the feed blend tank and separates liquid from the particulate biodegradable organic waste. A thermal hydrolysis reactor receives the particulate biodegradable organic waste from the first liquid/solid separator. A second liquid/solid separator receives solubilized organic material and residual solids from the thermal hydrolysis reactor for separating the solubilized organic material from the residual solids. A recirculating conduit conveys the solubilized organic material to the feed blend tank. A composter may be provided to receive residual solids from the second liquid/solid separator. An elutriation or washing device may be operatively associated with the second liquid/solid separator for removal of salts from the residual solids. A chemical supply may be operatively associated with the feed blend tank for providing a base to the particulate biodegradable organic waste prior to hydrolysis. The anaerobic reactor may be an upflow anaerobic sludge blanket reactor.

The method of the present invention provides an economically feasible and environmentally sound system for processing any particulate biodegradable organic waste material, including but not limited to particulate food waste, wastewater treatment biosolids, yard and garden ("green") waste, and source separated organic municipal solid waste. The method and apparatus provides a significant reduction in the volume of particulate biodegradable organic waste while yielding the further advantage of production of a methane rich gas. Residual solids from the process can be composted to produce a soil amendment or other value added byproduct, may be incinerated with favorable energy recovery or landfilled at a significant savings in volume requirements. Separation of solids from the solubilized organics allows for more efficient anaerobic digestion, which allows for smaller anaerobic digesters, less costly digesters and shorter retention times while still maximizing production of valuable methane gas.

DETAILED DESCRIPTION OF THE INVENTION

Figure 1:
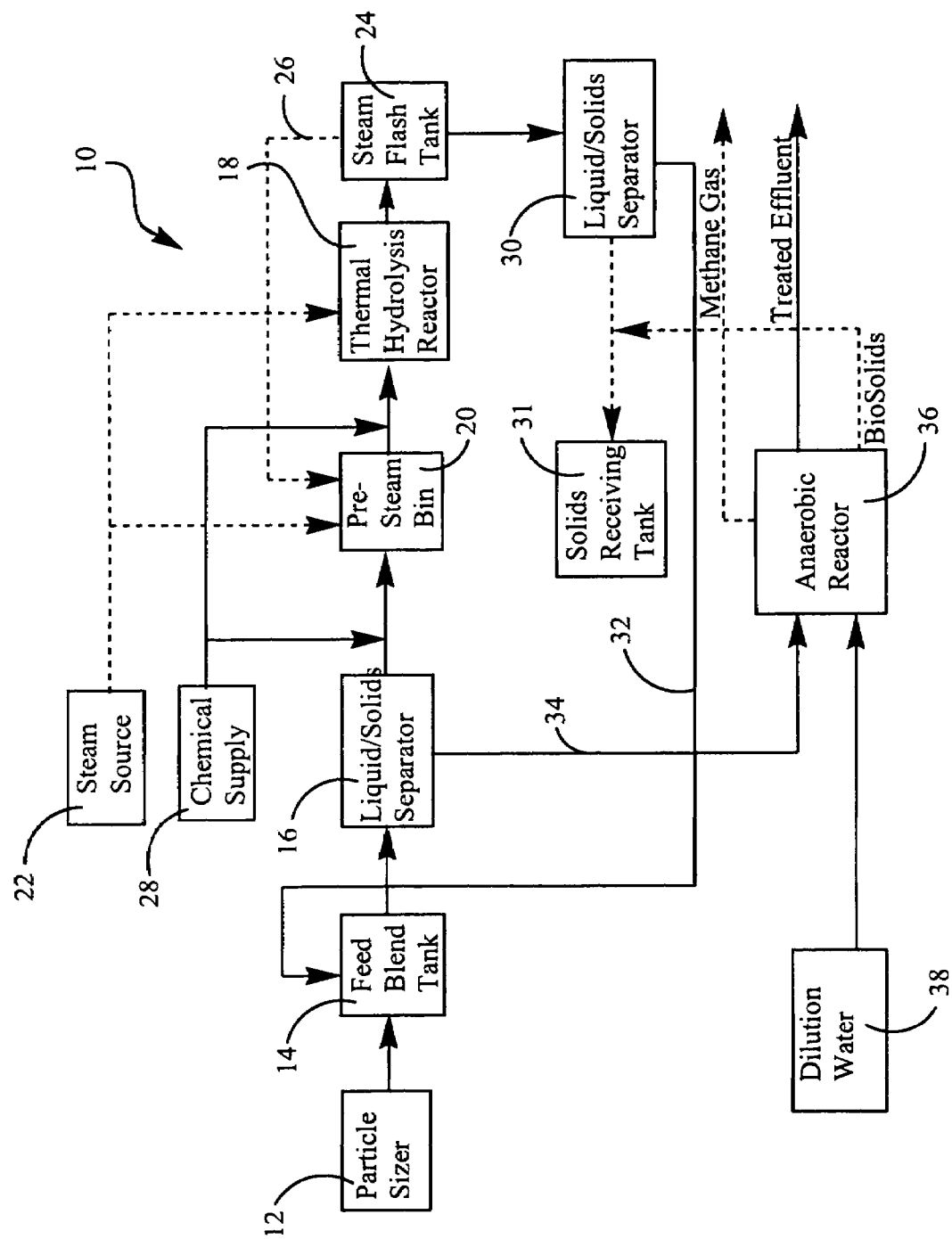
FIG. 1 is a schematic block diagram of a first embodiment of the instant invention.

A first embodiment of an apparatus for thermal hydrolysis and anaerobic treatment of particulate biodegradable organic waste 10 is illustrated schematically in FIG. 1. A particle sizer 12, which may be a shredder or grinder, receives particulate biodegradable organic waste to be treated and sizes the waste to a particle size of between ¼"-2". The particle sizer may be any suitable device for producing the desired sized particles known to the art. A feed blend tank 14 receives the sized particulate biodegradable organic waste from the particle sizer 12. The feed blend tank 14 may also be used to settle and separate higher specific gravity materials. The feed blend tank 14 may include a suitable agitator for mixing the particulate biodegradable organic waste for reasons that will become clear below.

A first liquid/solid separator 16 receives the particulate biodegradable organic waste from the feed blend tank 14 and separates liquid from the particulate organic waste. The first liquid/solid separator 16 may be a screw press, centrifuge or any other liquid/solid separator known to the art. A thermal hydrolysis reactor 18 receives the dewatered particulate biodegradable organic material for the purpose of solubilizing the particulate organics. In the preferred embodiment illustrated in FIG. 1, a pre-steaming bin 20 first receives the dewatered particulate biodegradable organic waste and steam from a steam source 22 is introduced to the pre-steaming bin to preheat the particulate biodegradable organic waste. From the pre-steaming bin 20 the material moves to the steam hydrolysis reactor 18. There, additional steam from the steam source 22 is added and thermal hydrolysis is performed at a temperature of about 130° C. and preferably at least about 170° C. and at or above the saturated water vapor pressure to produce a slurry including solubilized organic material and residual solids. The temperature range may be from about 130°-225° C. and the pressure may range from 46.1 psig to 370 psig. The hydrolysis is performed at a temperature, pressure and period of time which maximizes the amount of particulate biodegradable organic waste that is solubilized while optimizing the dewatering properties of residual solids and minimizing the production of ammonia and soluble organic compounds recalcitrant to biodegradation. Thus, there can be some variation in the given temperature and pressure ranges provided the goal of maximizing one or more of these objectives is met. The solubilized organic material and residual solids flow to the steam flash tank 24 where steam can be recovered for reuse and recycle to the pre-steaming bin 20 using known condensers through conduit 26 to preheat the particulate biodegradable organic waste prior to steam hydrolysis. While the preferred embodiment contemplates the thermal hydrolysis having heat provided by direct addition of steam, the use of indirect steam heating or any other direct or indirect source of heating is considered to be within the scope of the invention.

A chemical supply 28 may be provided to provide chemicals to the particulate organic waste prior to thermal hydrolysis to both promote hydrolysis and dewatering of the residual solids. Preferred chemicals may be either an acid or a base. Acids that can be used include, but are not limited to, HCl, $HNO_3$, sulfites, bisulfites and sulfates such as $H_2SO_4$. Bases that may be used may include any water soluble hydroxide including, but not limited to, NaOH, KOH, $Ca(OH)_2$ and $Mg(OH)_2$, with KOH currently being preferred. In a preferred embodiment, bases are used to provide alkalinity and maintain a favorable pH environment where the solubilized organics are subsequently subject to an anaerobic treatment process, as will be described below.

The thermal hydrolysis reactor 18 described above is a continuous feed reactor. Alternatively, and not illustrated, a batch type hydrolysis process may be used. In such a process, a feed bin replaces the pre-steaming bin 20 and the pre-steaming and hydrolysis functions are all accomplished in a single batch reactor in which the pH, temperature, pressure and residence time conditions are maintained as needed to provide the desired level of organic particulate matter solubilization.

Solubilized organics and residual solids flow to a second liquid/solid separator 30. As with the first liquid/solid separator 16, the second liquid/solid separator 30 may be any known separator such as a screw press or high solids centrifuge. The liquid/solid separator chosen will depend upon the residual particulate properties and the need to mitigate any odor concerns. If removal of salt or other water soluble contaminants from the residual solids is desired, washing/elutriation may be incorporated into the liquid/solid separation step. The dewatered residual solids are then delivered to a solids receiving tank 31 from where they can be subjected to composing and used as a soil amendment or fertilizer, as will be discussed further below.

Liquids from the second liquid/solid separator 30 are recycled via conduit 32 to the feed blend tank 14 for exchange of residual heat in the solubilized liquids from the hydrolysis reaction with the particulate biodegradable organic waste. This heat exchange may be accomplished with any known heat exchange device that keeps the material flows separate. Preferably, the solubilized liquids are mixed with the particulate biodegradable organic waste to effect the heat exchange. Thereafter, as described above, liquids, including the solubilized organics are separated from the particulate biodegradable organic waste by the first liquid/solid separator 16. The separated liquids flow through conduit 34 to an anaerobic reactor 36. If necessary or desired, dilution water from a source 38 may be added to the anaerobic reactor 36. The dilution water may be a secondary wastewater treatment plant effluent or any other suitable source of dilution water. Methane rich gas is captured from the anaerobic reactor and used for energy recovery. Treated effluent from the anaerobic reactor may be disposed in any suitable manner, including delivery to a conventional wastewater treatment plant. The liquid for anaerobic treatment may require disposal in a conventional wastewater treatment plant. As a condition to discharge to the receiving environment, limitation may be placed on the quantity or concentration of total oxygen demand of the residual organic component of the effluent, including non-degradable soluble organic compounds (measured as chemical oxygen demand (COD), total oxygen demand (TOC), or other analytical measure of residual organic material and ammonia. Therefore, it may be important to operate the thermal process of the invention in such a manner as to minimize the formation of soluble organic compounds recalcitrant to biodegradation as well as ammonia. Finally, biosolids recovered from the anaerobic reactor 36 may be combined with the dewatered residual solids in the solids receiving tank 31 for composing, combustion to produce energy, or other disposal.

Both mesophilic and thermophilic anaerobic processes may have application to this invention. Anaerobic processes operating in the mesophilic temperature range may be able to achieve higher degrees of methanization and process stability than those operating in the thermophilic temperature range. Several known process configurations, including but not limited to anaerobic contact, anaerobic filter, anaerobic fluid bed, upflow anaerobic sludge blanket (UASB), anaerobic membrane bioreactors, and hybrids of these anaerobic configurations, can be used with the method and apparatus of this invention for treatment of the hydrolysis liquor. Of these, the UASB configuration, particularly the ultra-high rate reactors developed and licensed by several suppliers that are capable of operating at inorganic loading in the range of 20-35 kg $COD/m^3/day$ are likely to be the most functional and cost effective. Representative suppliers and their models include: Biothane Corporation's Biobed™ and Paques BV's Internal Circulation Upflow Anaerobic Sludge Blanket Reactor (IC-UASB). Considering the concentration of the dissolved organics and probable ammonia concentration of the hydrolysis liquor, dilution will be required before anaerobic treatment. As discussed above, in lieu of fresh water, wastewater secondary treatment effluent would be an acceptable and economical source of dilution water.

Figure 2:
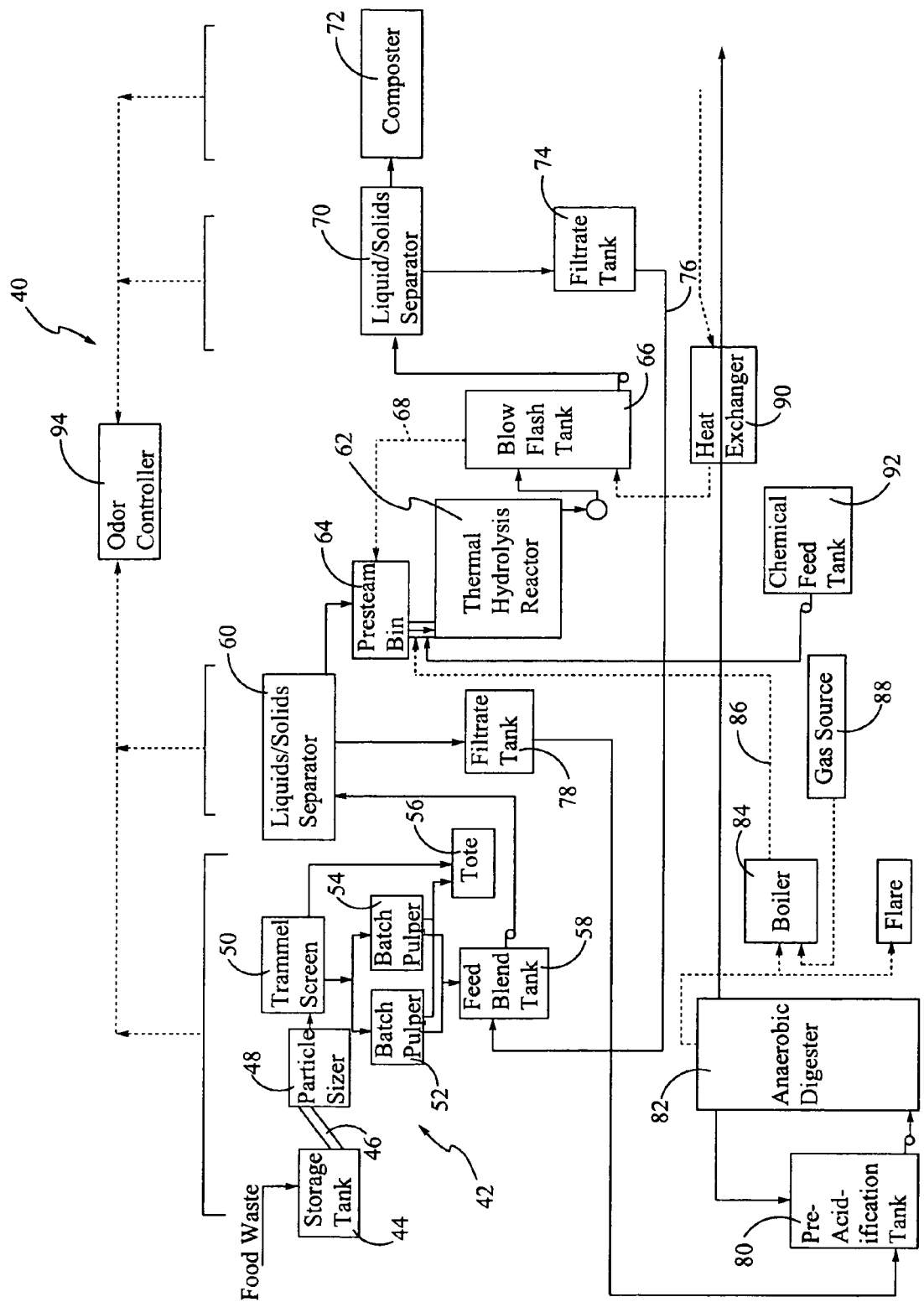
FIG. 2 is a schematic block diagram of a second embodiment of the instant invention.

A second embodiment of the apparatus for thermal hydrolysis and treatment of particulate biodegradable organic waste 40 is illustrated in FIG. 2. This embodiment is similar to the first embodiment of an apparatus for thermal hydrolysis and treatment of particulate biodegradable organic waste 10 discussed above with respect to FIG. 1, but has several enhancements. At the front end of the apparatus, receiving and processing apparatus 42 for the particulate biodegradable organic wastes are provided. This equipment is intended for breaking and removal or shredding of plastic bags; removal of other contaminants such as glass, wood, paper, plastics, and metal by screening, gravity, magnetic and/or manual separation; sizing and shredding and blending with waste biosolids. The receiving and processing apparatus 42 includes a food waste receiving and storage tank 44 connected by a conveyor 46 or other suitable transfer equipment to a particle sizer 48, which may be a grinder or a shredder. Material from the particle sizer 48 is conveyed to a trommel screen 50. Material passing the trommel screen 50 is fed to a pair of batch pulpers 52, 54 which help screen for inorganic wastes which are output to a landfill waste tote 56. In a like manner, inorganic materials trapped by the trommel screen 50 are deposited in the landfill waste tote 56. Organic materials from the batch pulpers 52, 54 are delivered to the feed blend tank 58. These materials are then conveyed to a first liquid solid separator 60 which may be a screw press, high solid centrifuge or other known liquid solid separator.

The separated solids are delivered to a continuous hydrolysis apparatus 62. Between the continuous hydrolysis apparatus 62 and the first liquid/solid separator 60 is preferably a pre-steaming bin 64 for preheating the particulate biodegradable organic waste. Following treatment in the continuous hydrolysis apparatus 62, solubilized organic materials and residual solids are output to a blow tank 66. Recovered steam is delivered by conduit 68 to the pre-steaming bin 64 to preheat the particulate biodegradable organic waste. The solubilized organic materials and residual solids pass from the blow tank 66 to a second liquid/solid separator 70 which may be of the same type as the first liquid/solid separator 60. The residual solids may then be output to a composing system 72 such as the C:N Composing Systems™ of CH2M HILL, Inc., or any other suitable composing system. The C:N Composing Systems™ is disclosed in U.S. Pat. No. 6,383,803 entitled "Portable Composing System with Reconfigurable Air Flow", which is incorporated by reference in its entirety herein. Alternatively, the solids may be suitable as a fuel or disposed of in a conventional landfill.

The separated liquids, including the solubilized organic material, pass through a residual filtrate tank 74 and are then recycled via conduit 76 to the feed blend tank 58 where these liquids are used to preheat the particulate biodegradable organic waste. As discussed with respect to the first embodiment, this may be done using any heat exchanger that does not mix the material flows. Preferably, however, the liquids are mixed with the particulate biodegradable organic waste.

The solubilized organics and other liquids are removed from the particulate biodegradable waste at the first liquid/solid separator 60 as described above and output to digester feed filtrate tank 78. From there, the liquids flow to a pre-acidification tank 80 and from there to an anaerobic reactor apparatus 82 which, in the preferred embodiment, is an ultra-high rate UASB reactor. The preacidification tank 80 may not be necessary if the complex organics (e.g., carbohydrates) in the solubilized liquid are largely converted into organic acids in the continuous hydrolysis apparatus 62. Methane rich gas produced in the anaerobic reactor 82 may be used in biogas/steam boiler 84 to generate the steam used in the continuous hydrolysis system 62 and conveyed thereto by conduit 86. Auxiliary natural gas or propane may be provided to the biogas/steam boiler from a source 88. Effluent from the reactor 82 is preferably run through a heat exchanger 90 where its latent heat is used to preheat dilution water, which may include municipal wastewater treatment plant effluent, which is used for salt elutriation and/or dilution of the residual solids prior to introduction into the composing system 72. As with the first embodiment 10 discussed in FIG. 1, a chemical supply 92 may provide an acid or a base to the thermal hydrolysis apparatus 62 to enhance hydrolysis and dewaterability.

In the preferred embodiment of FIG. 2, an odor control system 94 can be provided in operative association with the receiving and processing apparatus 42, the first liquid/solid separator 60, the second liquid/solid separator 70 and the composing system 72. The odor control system 94 is preferably a BIOCLEAN™ biofilter system as disclosed in U.S. Pat. No. 6,540,312, issued Apr. 1, 2003, entitled "Modular Biofilter Unit," which is incorporated in its entirety herein by reference, but can be any other known odor control device or system.

If the particulate biodegradable organic waste contains high concentrations of salt, washing the residual solids remaining after hydrolysis to remove the salt may be necessary to produce a compost product that can be successfully used as a soil amendment or fertilizer. In one embodiment, this is accomplished by passing the slurry coming out of the blow tank 66 over a screening and concentrating device used in conjunction with the second liquid/solids separation device 70. The hydrolysis liquor passes through the screen and is fed to the filtrate tank 74, while the residual solids are retained on the screen. The residual solids are then sprayed with water, which may be provided from a wastewater treatment system effluent, to further enhance salt removal. The residual solids are then dewatered as described above and the wastewater is flowed to the residual filtrate tank 74.

EXAMPLES

The following examples are provided for illustrative purposes only and are not intended to limit the scope of the invention.

Test Material:

A number of bench tests were conducted to evaluate the efficacy of hydrolyzation under various operating conditions and anaerobic digestion of the solubilized organics under different operating conditions. The feed stocks used in the examples below were taken from food waste obtained from Korean restaurants in the Seattle metropolitan area. Approximately 80 gallons of food waste was collected from three Korean restaurants and maintained in cold storage. Two heavy-duty household ("garbage") grinders were used to grind the particulate waste to approximately 3/16" or less sized particles. After the food waste was ground, it was put into two 50-gallon coated steel drums designated as Sample A and Sample B. Sample A was used for the first 9 hydrolysis treatability tests (cooks 1-9) and Sample B was used for cooks 10-19, which are described in greater detail below. The samples were analyzed to determine the crude protein, crude fiber, crude fat and ash content and this data is presented in Table 1 below:

TABLE 1

| Description | Crude Protein (%) | Crude Fiber (%) | Crude Fat (%) | Ash (%) |
|---|---|---|---|---|
| Sample A | 18.7 | 14.2 | 18.8 | 6.87 |
| Sample B | 18.2 | 14.7 | 17.9 | 6.62 |

Thermal Hydrolysis:

The thermal hydrolysis treatability study was conducted using a bench-scale reactor system manufactured by Aurora Technical Products (of Savona, British Columbia). The test equipment used an electrically heated, 11.6-liter, stainless steel pressure vessel equipped with an agitator, an oxygen injection system, a headspace vent system to relieve vapor generated during the "cook" and at completion of the cook during cool down, and an air-operated drain valve. The hatch digester also was connected by a valve to an adjacent "blow tank" to transfer the digester contents at the end of an oxygen cook, using pressure in the reactor. The reactor had a pressure rating of 150 pounds psig (at a saturation temperature of 185° C.).

For the purpose of the study, the Aurora batch digester system was modified as follows. The headspace vent system was connected to a coiled copper tube placed in an approximately 20-liter plastic bucket containing ice and water. This modification provided means of condensing capturing and measuring the volume of vapor produced during digestion and during pressure relief at the end of the cook and providing a sample of the condensate for chemical characterization. To minimize vapor loss, the "blow tank" was not used to collect the reactor contents at the end of the cook. Instead, the digester was emptied through the air-rain operated drain valve at the bottom of the reactor, after all but about 2 psig of pressure had been relieved from the digester through the headspace vent system.

Figure 3:
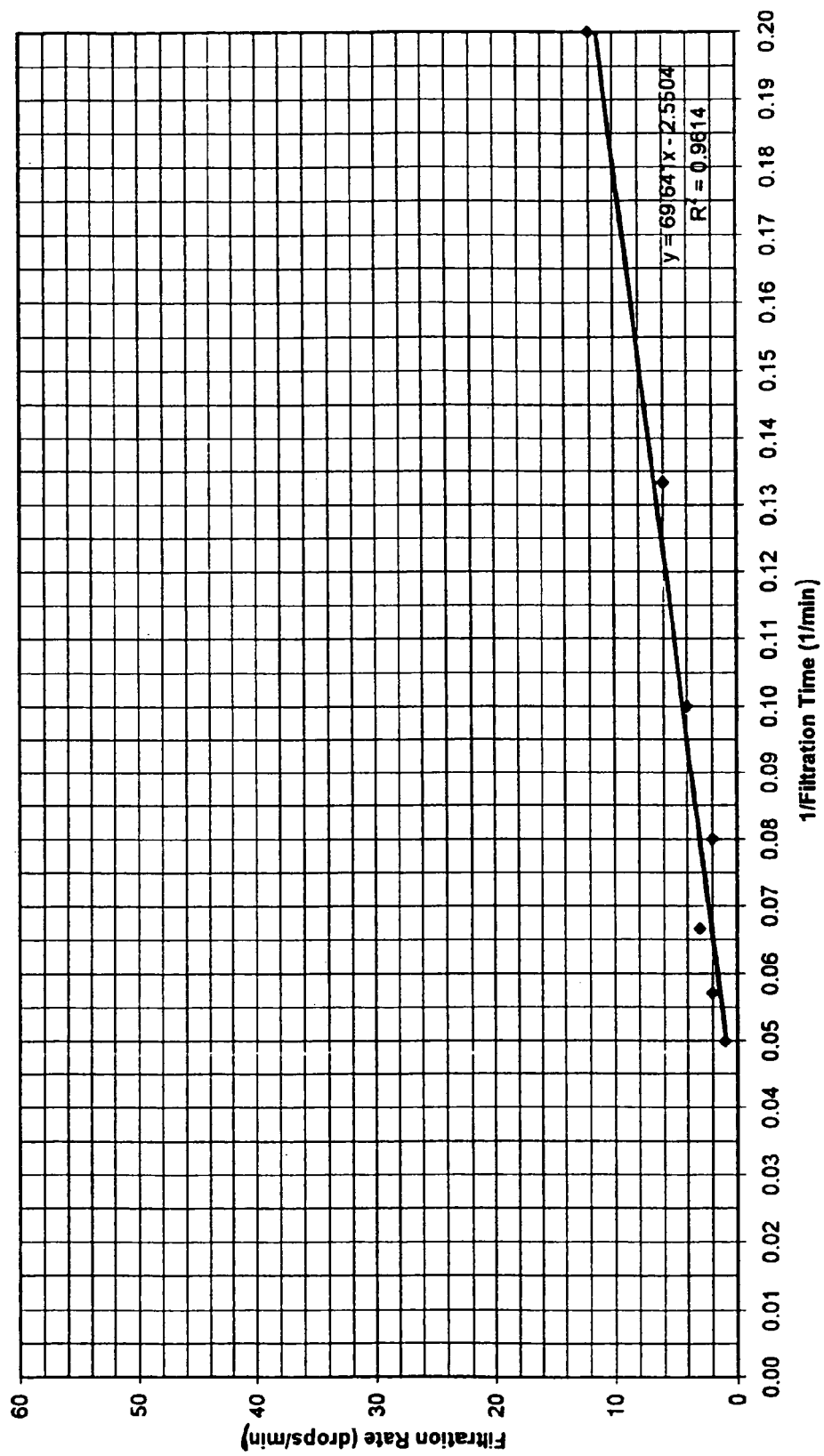
FIG. 3 is a graph of the filtration rate versus time for cook number 19 of the examples.

Residual unhydrolized solids dewatering or liquid/solid separation was performed using a wood pulp dewatering apparatus consisting of a 12-inch Buchner funnel connected to a laboratory vacuum supply and Wattman 40 filter paper. To compare the relative dewaterabibty of residual solids from various digester operating conditions, a standardized vacuum filtration testing procedure was developed, which used a 4-inch Buchner funnel and Wattman 40 filter paper and was used on small samples extracted from the hydrolysis reactor. The relative dewaterability of the residual solids produced under differing digestion conditions was determined. This was done by competing the slope of the straight line produced from plotting the drainage rate versus reciprocal time (drops per minute versus 1/drainage time) with its intercept with the x-axis. A lower (flatter) slope indicated that the liquid drained more easily from the solids. This is illustrated in FIG. 3, which is a plot of filtration rate (drops/minute) versus 1/filtration time (1/min.) for Cook Number 19 described in Table 2 below. The time at which the drainage was predicted to stop was determined from the x-axis intercept. Each filtration was stopped after 30 minutes. The filter cake was weighed, dried to constant weight, reweighed to determine the relative moisture content of the residual solids.

Initially, the hydrolysis was attempted at 130° C. and was found insufficiently efficient. Thereafter, the hydrolysis was done at at least 170° C. The hydrolysis reactor cooking conditions for 19 test runs are summarized in Table 2 below:

TABLE 2

| Cook No. | Feed Batch | Temp. (° C.) | Cook Time (minutes) | Chemical Addition | Comments |
|---|---|---|---|---|---|
| 1 | A | 170 | 60 | None | |
| 2 | A | 190 | 60 | None | Run aborted, could not hold temperature |
| 3 | A | 170 | 15 | None | |
| 4 | A | 170 | 120 | None | |
| 5 | A | 170 | 60 | 1% NaOH[a] | |
| 6 | A | 170 | 60 | 5% NaOH | Hydrolysis liquor solids were not filterable |
| 7 | A | 170 | 60 | 1% Ca(OH)$_2$[b] | Hydrolysis liquor lost in discharge from reactor |
| 8 | A | 170 | 60 | 5% Ca(OH)$_2$ | Hydrolysis liquor solids were not filterable |
| 9 | A | 170 | 60 | 5% KOH[c] | |
| 10 | B | 170 | 15 | None | |
| 11 | B | 170 | 60 | 1% Ca(OH)$_2$ | |
| 12 | B | 170 | 60 | 1% H$_2$SO$_4$[d] | |
| 13 | B | 170 | 60 | 2.5% H$_2$SO$_4$ | Run aborted, heater failure |
| 14 | B | 170 | 60 | 2.5% H$_2$SO$_4$ | |
| 15 | B | 170 | 240 | None | |
| 16 | B | 170 | 240 | 5% KOH | |
| 17 | B | 170 | 240 | 5% H$_2$SO$_4$ | |
| 18 | B | 170 | 60 | 2.5% KOH | |
| 19 | B | 170 | 60 | 0.96% KOH | |

[a]Sodium hydroxide
[b]Potassium hydroxide
[c]Calcium hydroxide
[d]Sulfuric acid The solubilization of the 14 cooks that provided usable data is summarized in Table 3 below:

TABLE 3

| Cook No. | Feed Batch | Cook Conditions (temp./time/chemical) | pH | Solubilized Total Feed Solids (%) | Solubilized Volatile Feed Solids (%) | Filter Cake Solids (%) | Feed Vol. ReducTion (%) |
|---|---|---|---|---|---|---|---|
| 3 | 1 | 170/15/None | 4.23 | 65.2% | 67.8% | 50.0% | 84.0% |
| 10 | 2 | 170/15/None | 4.04-4.3 | 61.9% | 63.8% | 41.8% | 79.2% |
| 1 | 1 | 170/60/None | 4.30 | 58.0% | 58.9% | 42.8% | 77.4% |
| 4 | 1 | 170/120/None | 4.47 | 69.5% | 72.6% | 52.8% | 86.7% |
| 15 | 2 | 170/240/None | 3.64-3.92 | 66.4% | 64.4% | 48.5% | 84.2% |

TABLE 3-continued

| Cook No. | Feed Batch | Cook Conditions (temp./time/ chemical) | pH | Solubilized Total Feed Solids (%) | Solubilized Volatile Feed Solids (%) | Filter Cake Solids (%) | Feed Vol. ReducTion (%) |
|---|---|---|---|---|---|---|---|
| 5 | 1 | 170/60/1% NaOH[a] | 4.90 | 51.2% | 52.6% | 44.8% | 74.9% |
| 19 | 2 | 170/60/0.96% KOH[b] | 3.87-3.95 | 65.9% | 62.3% | 50.5% | 87.3% |
| 18 | 2 | 170/60/2.5% KOH | 4.02-4.25 | 66.9% | 63.2% | 40.3% | 83.8% |
| 9 | 1 | 170/60/5% KOH | 4.52-5.15 | 69.9% | 71.5% | 44.4% | 84.4% |
| 16 | 2 | 170/240/5% KOH | 4.45-4.70 | 73.3% | 70.0% | 42.1% | 83.8% |
| 11 | 2 | 170/60/1% Ca(OH)$_2$[c] | 3.75-3.85 | 59.5% | 62.1% | 39.1% | 76.4% |
| 12 | 2 | 170/60/1% H$_2$SO$_4$[d] | 3.35-3.85 | 58.4% | 60.4% | 45.8% | 79.3% |
| 14 | 2 | 170/60/2.5% H$_2$SO$_4$ | 3.15-3.6 | 57.6% | 55.0% | 54.4% | 82.2% |
| 17 | 2 | 170/240/5% H$_2$SO$_4$ | 2.63-2.9 | 62.7% | 55.5% | 51.0% | 84.9% |

[a]Sodium hydroxide
[b]Potassium hydroxide
[c]Calcium hydroxide
[d]Sulfuric acid It is not clear from the data whether lengthening the time at temperature cooking over the range of 15-240 minutes significantly increased the degree of solubilization. This observation may be affected, however, by the 1-2.5 hours that were required to bring the laboratory-scale batch reactor to temperature. Between 15-60 minutes in a continuous reactor operating at about 170° C. or higher is likely to be adequate time and temperature to achieve near maximum solubilization.

Filter cake dryness and relative filterability data resulting from the use of the 4-inch Buchner funnel standardized test described above are summarized in Table 4 below:

TABLE 4

| Cook No. | Feed Batch | Cook Conditions (temp./time/ chemical) | pH | Filter Cake Solids (%) | Filter Cake Ash (%) | Relative Filterability Slope (drops) | Relative Filterability Time (min.) |
|---|---|---|---|---|---|---|---|
| 10 | B | 170/15/None | 4.04-4.3 | 41.8% | 13.9% | 179 | 63.8 |
| 4 | A | 170/120/None | 4.47 | 52.8% | 18.5% | 262 | 32.6 |
| 15 | B | 170/240/None | 3.64-3.92 | 48.5% | 3.9% | 118 | 32.6 |
| 19 | B | 170/60/0.96% KOH[a] | 3.87-3.95 | 50.5% | 2.2% | 79 | 24.4 |
| 18 | B | 170/60/2.5% KOH | 4.02-4.25 | 40.3% | 6.3% | 340 | 24.4 |
| 9 | A | 170/60/5% KOH | 4.52-5.15 | 44.4% | 13.9% | 571 | 70.5 |
| 16 | B | 170/240/5% KOH | 4.45-4.70 | 42.1% | 8.9% | 290 | 51.4 |
| 11 | B | 170/60/1% Ca(OH)$_2$[b] | 3.75-3.85 | 39.1% | 15.1% | 220 | 72.5 |
| 12 | B | 170/60/1% H$_2$SO$_4$[c] | 3.35-3.85 | 45.8% | 13.8% | 113 | 37.4 |
| 14 | B | 170/60/2.5% H$_2$SO$_4$ | 3.15-3.6 | 54.4% | 3.8% | 176 | 37.9 |
| 17 | B | 170/240/5% H$_2$SO$_4$ | 2.63-2.9 | 51.0% | 4.5% | 138 | 24.5 |
| 3 | A | 170/15/None | 4.23 | | 16.1% | | |
| 1 | A | 170/60/None | 4.30 | | 11.1% | | |
| 5 | A | 170/60/1% NaOH[d] | 4.90 | | 11.8% | | |

[a]Potassium hydroxide
[b]Calcium hydroxide
[c]Sulfuric acid
[d]Sodium hydroxide On the basis of the comparison of the slope and x-axis intercept determined from plotting the filtration rate versus reciprocal time, filterability tended to improve when the hydrolysis liquor pH was at or below 4.0. The best filterability, however, was achieved when a small amount of KOH (approximately 1% as dry weight of feed solids) was added to the batch test.

Anaerobic Digestion Treatability:

A laboratory-scale UASB system used for the continuous-feed anaerobic treatability study consisted of a feed tank, feed pump, UASB reactor containing dense granular anaerobic biosolids, recycle pump, gas collection bag and an effluent tank, all connected by plastic tubing. The UASB reactor consisted of a clear, polyvinyl chloride (PVC) column 10.2 centimeters (cm) (4 inches) in diameter and 55.8 cm (20 inches) in height, fitted with a conical bottom and having a total volume of 4.3 liters (L). Liquid and biosolids occupied 3.6 L, and the remaining 0.7 L served as a headspace for gas collection. The UASB was fitted with inlet ports for feed and recycle, a bottom funnel to distribute the feed and recycle flow, and outlet ports from which to draw/recycle, effluent, and biogas.

The UASB was initially charged with 0.9 L of granular anaerobic biosolids obtained from a full-scale UASB wastewater treatment system at the Penford Starch Processing Plant in Richland, Wash. The granular biosolids, as received, had a total solids concentration of 93.5 g/L and a volatile solids concentration of 61.6 g/L (65.9% volatile).

Feed flow and recycle rate were maintained at nearly constant rates during the continuous-feed phase of the anaerobic treatability study. The UASB was targeted to operate at 5 sequential volumetric loading rates (VLRs): 4, 8, 16, 30 and 36 grams of influent soluble COD per liter of reactor volume per day (g SCOD applied/L-d). To achieve these target organic loading rates, feed was prepared in 2-day batches from hydrolysis liquor and diluted with deionized water to result in the desired SCOD concentration. Supplemental inorganic macro- and micro-nutrients and alkalinity were added to the feed in proportion to the SCOD concentration to ensure adequate inorganic nutrient availability. The target VLR, actual VLR, calculated food applied-to-volatile mass ratios (Fa/Mv) on both the soluble COD and soluble $BOD_5$ applied basis, and a hydraulic retention time (HRT) in the reactor based on feed flow for the five organic loading conditions were evaluated as indicated in Table 5 below:

TABLE 5

| Parameter | Units | Period 1 | Period 2 | Period 3 | Period 4 | Period 5 |
|---|---|---|---|---|---|---|
| Target VLR | (g SCOD/L-d) | 4 | 8 | 16 | 30 | 36 |
| Actual VLR | (g SCOD/L-d) | 3.48 | 7.57 | 14.8 | 24.2 | 31.1 |
| Fa/Mv - TCOD applied | (g/g-d) | 0.18 | 0.36 | 0.64 | 0.99 | 1.73 |
| Fa/Mv - $TBOD_5$ applied | (g/g-d) | 0.06 | 0.16 | 0.24 | 0.35 | 0.75 |
| HRT | (hours) | 9.96 | 8.57 | 8.80 | 9.01 | 9.17 |

Table 6 summarizes the average COD and $BOD_5$ removal performance of the UASB treatment system determined for the five organic loading conditions evaluated:

TABLE 6

| Parameter | Units | Period 1 | Period 2 | Period 3 | Period 4 | Period 5 |
|---|---|---|---|---|---|---|
| Actual VLR | (g SCOD/L-d) | 3.48 | 7.57 | 14.8 | 24.2 | 31.1 |
| TCOD in | (mg/L) | 1,796 | 3,412 | 6,903 | 12,343 | 15,440 |
| TCOD out | (mg/L) | 523 | 908 | 1,811 | 4,230 | 9,334 |
| TCOD removed | (%) | 71.9 | 73.8 | 73.4 | 66.3 | 30.8 |
| SCOD in | (mg/L) | 1,436 | 2,704 | 5,402 | 9,061 | 11,880 |
| SCOD out | (mg/L) | 381 | 761 | 1,535 | 2,859 | 7,970 |
| SCOD removed | (%) | 73.3 | 71.6 | 71.5 | 68.2 | 31.6 |
| $TBOD_5$ in | (mg/L) | 645 | 1,514 | 2,688 | 4,369 | 6,267 |
| $TBOD_5$ out | (mg/L) | 71 | 133 | 258 | 681 | 4,681 |
| $TBOD_5$ removed | (%) | 89.5 | 91.4 | 90.3 | 85.7 | 25.4 |
| $SBOD_5$ in | (mg/L) | 575 | 1,144 | 2,224 | 3,364 | 5,744 |
| $SBOD_5$ out | (mg/L) | 43 | 103 | 155 | 555 | 4,511 |
| $SBOD_5$ removed | (%) | 92.0 | 91.1 | 93.3 | 84.5 | 22.7 |
| $BOD_5$ removed (Tin-Sout)[a] | (%) | 92.9 | 93.3 | 94.2 | 88.2 | 28.7 |
| $TBOD_5$ rem/ TCOD rem | (ratio) | 0.451 | 0.552 | 0.477 | 0.455 | 0.260 |
| $SBOD_5$ rem/ SCOD rem | (ratio) | 0.504 | 0.536 | 0.535 | 0.453 | 0.315 |
| $SBOD_5$ in/ SCOD in | (ratio) | 0.400 | 0.423 | 0.412 | 0.371 | 0.484 |
| $SBOD_5$ out/ SCOD out | (ratio) | 0.114 | 0.135 | 0.101 | 0.194 | 0.566 |
| TSS in | (mg/L) | 146 | 302 | 517 | 380 | 390 |
| TSS out | (mg/L) | 16.1 | 44.0 | 127.3 | 512 | 1,137 |
| VSS in | (mg/L) | 146 | 304 | 500 | 380 | 366 |
| VSS out | (mg/L) | 18.0 | 28.0 | 114 | 443 | 965 |
| VSS/TSS in | (ratio) | 1.000 | 1.007 | 0.966 | 1.000 | 0.938 |
| VSS/TSS out | (ratio) | 1.116 | 0.636 | 0.895 | 0.865 | 0.849 |
| $SGPR^b$ - SCOD removed | (L/g SCODr) | 0.266 | 0.411 | 0.484 | 0.533 | 0.944 |
| SGPR - $BOD_5$ (Tin-Sout) | (L/g $BOD_5$r) | 0.466 | 0.566 | 0.744 | 0.864 | 2.229 |

Biogas Production:

Biogas production normalized to SCOD and $BOD_5$ removal (referred to a specific gas production rate) (SPGR)), after initial acclimation period, tended to increase from 0.4 to more than 0.5 L/g SCOD removed with increasing volumetric organic loading rate, until the USAB failed due to hydraulic over loading and washout of biomass at 31 g SCOD/L-d. The methane ($CH_4$), carbon dioxide ($CO_2$) and hydrogen sulfide ($H_2S$) contents of the biogas were determined several times during the course of the continuous treatability study and are summarized in Table 7 below:

TABLE 7

| Feed Stock | VLR (g SCOD/L-d) | $CH_4$ (%) | $CO_2$ (%) | $H_2O$ (%) | $H_2S$ (%) | $H_2S$ ($ppm_v$) |
|---|---|---|---|---|---|---|
| Composite 1 | 13.94 | 63.97 | 32.00 | 4.00 | 0.03 | 310 |
| Composite 2 | 15.50 | 61.35 | 34.50 | 4.00 | 0.16 | 1,550 |
| Composite 3 | 24.66 | 53.11 | 42.67 | 4.00 | 0.23 | 2,283 |
| Composite 4 | 31.08 | 18.29 | 77.33 | 4.00 | 0.37 | 3,733 |

What is claimed is:
1. An apparatus for treating particulate biodegradable organic waste comprising:

a thermal hydrolysis reactor receiving the particulate biodegradable organic waste for performing thermal hydrolysis at a temperature above about 130° C. and a pressure at or above the saturated water vapor pressure to produce a slurry including solubilized organic material and residual solids;

pH adjustment means for adjusting the pH of the particulate biodegradable organic waste as necessary to provide an acidic pH of greater than about 3.15 before thermal hydrolysis of the particulate biodegradable organic waste;

separating means receiving the solubilized organic material and residual solids for separating solubilized organic material from residual solids;

an anaerobic reactor configured to receive the solubilized organic material;

means for circulating the solubilized organic material from the separating means to the first separating means; and the anaerobic reactor being configured to receive liquid including the solubilized organic material from the separating means and not solubilized organic material directly from the second separating means.

2. A method of treating particulate biodegradable organic waste comprising:

a) adjusting the pH of the biodegradable organic waste as necessary to provide acidic pH of greater than 3.15;

b) subjecting the particulate biodegradable organic waste with an acidic pH to thermal hydrolysis at a temperature above about 130° C. and a pressure at about or above the saturated water vapor pressure to produce a slurry including solubilized organic material and residual solids;

c) separating the solubilized organic material from the residual solids; and d) subjecting the solubilized organic material to anaerobic digestion to produce a methane rich gas.

3. The method of claim 1 further comprising prior to step a), separating liquid from the particulate biodegradable organic waste.

4. The method of claim 1 further comprising:

a1) before step b), mixing the particulate biodegradable organic waste with the separated solubilized organic material of step c) to heat the particulate biodegradable organic waste;

a2) removing liquid, including the solubilized organic material, from the heated particulate biodegradable organic waste; and a3) subjecting the removed liquid of step a) to the anaerobic digestion of step d).

* * * * *